United States Patent [19]

Scherrer

[11] 4,124,603

[45] Nov. 7, 1978

[54] 4-(OR 5 OR 6 OR 7)CYANO-2-NITRO-3-PHENYLBENZOFURANS

[75] Inventor: Robert A. Scherrer, White Bear Lake, Minn.

[73] Assignee: Riker Laboratories, Inc., Northridge, Calif.

[21] Appl. No.: 851,857

[22] Filed: Nov. 16, 1977

Related U.S. Application Data

[60] Division of Ser. No. 724,572, Sep. 20, 1976, Pat. No. 4,067,993, which is a continuation-in-part of Ser. No. 616,274, Sep. 24, 1975, abandoned.

[51] Int. Cl.$^2$ ............................................. C07D 307/82
[52] U.S. Cl. ................................................ 260/346.22
[58] Field of Search .................................... 260/346.22

[56] References Cited

U.S. PATENT DOCUMENTS 3,862,134  1/1975  Scherrer ........................ 260/346.22

Primary Examiner—Henry R. Jiles
Assistant Examiner—Bernard Dentz
Attorney, Agent, or Firm—Cruzan Alexander; Donald M. Sell; Donald C. Gipple

[57] ABSTRACT

Optionally substituted 2-nitro-3-phenylbenzofuran-carboxylic acids which are active as antimicrobial agents, processes for their preparation and intermediates therefor are described.

11 Claims, No Drawings

4-(OR 5 OR 6 OR 7)CYANO-2-NITRO-3-PHENYLBENZOFURANS

This is a division of application Ser. No. 724,572 filed Sept. 20, 1976, now U.S. Pat. No. 4,067,993, which was a continuation-in-part of application Ser. No. 616,274, filed Sept. 24, 1975 now abandoned.

FIELD OF THE INVENTION

This invention relates to a class of 3-phenylbenzofuran compounds which are substituted on the 4, 5, 6, or 7 position of the benzo ring by a carboxylic acid group or an ester, amide, acyl halide or pharmaceutically acceptable salt thereof.

BACKGROUND OF THE INVENTION

3-Phenylbenzofuranalkanoic acids and -alkenoic acids and certain derivatives thereof have been reported, for example in U.S. Pat. Nos. 3,682,976 and 3,862,134 as having antiinflammatory acitivity. The compound 2-nitro-3-phenylbenzofuran has been reported, although no physiological activity has been reported prior to the present invention. Certain neutral 2-nitrobenzofurans are known as antibacterial agents, for example, see French Pat. No. 2,081,585 and several publications by Rene Royer, et al. Acidic compounds combining the structural features of the compounds of the present invention have not previously been described.

SUMMARY OF THE INVENTION

The present invention relates to optionally substituted 2-nitro-3-phenylbenzofurancarboxylic acids and esters, amides, acyl halides and pharmaceutically acceptable salts thereof which are active as antimicrobial agents.

It is therefore an object of the invention to provide compounds which are active antimicrobial agents.

It is a further object of the invention to provide processes for preparing the compounds of the invention.

It is a further object of the invention to provide a method for controlling microbes.

It is a further object of the invention to provide a method for controlling bacteria.

It is a further object of the invention to provide a method for controlling fungi.

It is a further object of the invention to provide a method for controlling protozoa.

It is a further object of the invention to provide a method for controlling trichomonads.

It is another object of the invention to provide antimicrobial compositions containing 2-nitro-3-phenylbenzofurancarboxylic acids and esters, amides, acyl halides and pharmaceutically acceptable salts thereof as active ingredients therein.

It is another object of the invention to provide novel intermediates in the preparation of the antimicrobial agenst of the invention and processes using the novel intermediates to prepare the active agents.

Still other objects of the invention will be made apparent by the following specification.

DETAILED DESCRIPTION OF THE INVENTION

The present invention relates to a class of compounds of the formula:

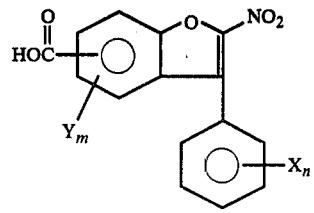

wherein X is fluorine, chlorine, lower alkyl or lower alkoxy, Y is methyl, methoxy, fluorine or chlorine and m and n are independently 0, 1 or 2, and esters, amides, acid halides and pharmaceutically acceptable salts thereof. When m or n is 0, the indicated ring positions are unsubstituted. The term "lower" whenever used in this specification indicates groups containing from one to four carbon atoms.

The free acids are ordinarily white or yellowish to brown crystalline or amorphous materials when purified. They are substantially insoluble in water or aliphatic hydrocarbons and are more soluble in lower alcohols, halogenated solvents, benzene, dimethylformamide and the like. The esters and amides are generally somewhat more soluble in organic solvents. The alkali metal salts have appreciable solubility in water and lower alcohols.

All of the compounds of the invention are active against bacteria and some are also active against other microorganisms, including fungi and protozoa, in vitro and topically. Thus, they can be used for disinfecting and sterilizing, for example of medical and dental equipment, as components of disinfecting solutions. The compounds are particularly useful as antibacterial agents. In general, the compounds are also active in vivo in animals. The free acids are presently preferred for many purposes due to their generally higher levels of antimicrobial activity in vitro. For applications in which water solubility is of importance, the salts are ordinarily used.

Presently preferred subclasses (due to their high degree of antimicrobial acitivity) are the compounds in which m and n are 0 and the compounds in which the four position of the benzofuran moiety is substituted by hydrogen. The preferred compounds are antimicrobial in vitro and in vivo, are active when administered orally and provide detectable and antimicrobially active blood levels in mammals. Some of them are active at concentrations of less than 1.0 µg/ml versus Streptococci. The particularly preferred compounds (which have broad spectra of antimicrobial activities and good therapeutic ratios, $LD_{50}/ED_{50}$) are 2-nitro-3-phenyl-7-benzofurancarboxylic acid,
2-nitro-3-phenyl-6-benzofurancarboxylic acid and
2-nitro-3-phenyl-5-benzofurancarboxylic acid.

Alkali metal, alkaline earth, aluminum, iron and other metal and amine salts are often the equivalents of the corresponding acid-form compounds, and offer advantages in solubility, absorption, persistence, formulation and the like. The salts are of particular interest for topical use, for example in opthalmic and dermatologic formulations. The alkali metal salts (e.g. the sodium and potassium salts) are presently preferred. The esters, amides and acyl halides are also useful for modifying solubility, persistence, absorption and other properties of the compounds under conditions of use. Examples of esters are ethyl, diethylaminoethyl, 2-hydroxyethyl, glyceryl, and methoxymethyl.

Among the other important subclasses of the compounds of the invention which are represented by specific examples herein, are lower alkyl esters, hydroxyalkyl esters and N,N-dialkylaminoalkyl esters, amides, e.g. dialkylaminoalkylamides, quaternary ammonium alkylamides, bis(2-hydroxyethyl)amides, glycine amides, carboxyphenylamides, and heterocyclic amides, sulfoethylamides, sulfamoylphenylamides, 5-tetrazolylamides.

The free acid compounds of the invention are prepared by several methods using known starting materials including:

A. directly nitrating the 2 position of a compound of the formula

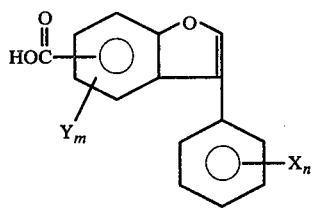

II

B. specifically halogenating the 2 position of a compound of formula II to form an intermediate compound of the formula

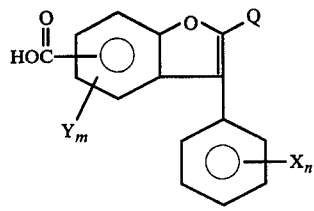

III wherein Q is bromine or iodine followed by selectively displacing the 2-halogen atom by a nitro group, or C. the acid hydrolysis of a corresponding compound of the formula

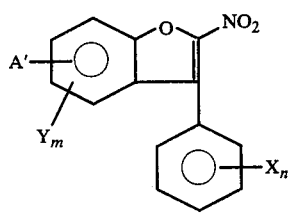

IV wherein A' is cyano, or a carboxylic ester group.

The direct nitration process (process A) can be carried out with fuming nitric acid in acetic acid or acetic anhydride or with dinitrogen tetroxide in an inert solvent such as dichloromethane. In order to avoid aromatic nitration, moderate temperatures of 0° to 30° C are generally used.

The halogenation step of process B may be bromination or iodination. The bromination can be carried out using bromine water, N-bromosuccinimide or preferably bromine in a suitable solvent such as dichloromethane or acetic acid. Bromination is carried out under mild conditions, e.g. 0° to 30° C to avoid aromatic bromination. The bromo compound may be isolated or used without isolation. Isolation may be carried out by extraction, precipitation by the addition of a solvent such as water, evaporation of volatile reaction components, etc. The iodination is carried out e.g. with molecular iodine in the presence of yellow mercuric oxide in an inert solvent such as benzene. Generally these reactions are carried out at about 25° to 125° C, for example at the reflux temperature of the solvent.

In the final step of process B, the 2-halo substituent can be displaced by means of selected nitrating agents, such as strong nitric acid solution, for example 70% aqueous nitric acid, dinitrogen tetroxide in e.g. acetic acid or dichloromethane solution or a mixture of sodium nitrite and a strong acid. When 70% nitric acid is used as the nitrating reagent for 2-halo derivatives, preferably about two to three moles each of sodium nitrite and nitric acid per mole of benzofuran is included. About four to twenty milliliters of acetic acid per gram of 2-halobenzofuran derivative is used, depending on its solubility. It is desired to maintain the dissolution of the 2-halobenzofuran derivative, the amount of acetic acid and the reaction temperature is adjusted to achieve this result readily. The reaction temperature is about 25° to 100° C, and preferably about 60° to 80° C when the halogen is bromine.

It has been found that a mixture of sodium nitrite, sulfuric acid and acetic acid will also nitrate the 2-halobenzofuran derivatives successfully in the 2-position. The 2-halobenzofuran derivative is dissolved in acetic acid to maintain solution (up to 20 ml per gram required) and concentrated sulfuric acid is added, from 2 to 10 milliliters per gram of benzofuran. Sodium nitrite is then added to the solution. From 2 to 5 moles of nitrite per mole of benzofuran derivative is used. The reaction temperature is about 20° to 100° C, and preferably about 55° C. The sodium nitrite can be replaced in this reaction by other metal nitrites such as potassium nitrite.

A combination of nitrogen tetroxide in an inert solvent in the presence of an alkene is one presently preferred nitration method according to process B, with acetic acid and dichloromethane as the preferred solvents. For example, 2 to 5 liters of acetic acid per mole of benzofuran or halobenzofuran derivative are generally used. At least one mole of nitrogen tetroxide per mole of benzofuran is used. The exact amount depends on the rate of reaction desired, the extent of volatilization and other physical losses and the amount of competitive addition to the added olefin. An alkene is preferably used with a 2-bromobenzofuran intermediate to remove the elements of $BrNO_2$ and minimize bromination as a side reaction. Cyclohexene is satisfactory for this use. Preferably equimolar amounts of alkene and nitrogen tetroxide are used. The olefin is chosen to be less reactive to $N_2O_4$ than the benzofuran but more reactive to $BrNO_2$ than the benzofuran. An acidic olefin, e.g. 3-cyclohexene carboxylic acid is advantageous when the nitrated product is neutral. The temperature of these reactions is generally about 0° to 80° C, preferably 20° to 45° C for bromine exchange and about 0° to 25° C for iodine exchange and direct nitration. When 2-iodobenzofurans are used, the olefin is not required (since the iodine is generally unreactive to the benzofuran under the reaction conditions) and only one-half mole of $N_2O_4$ is theoretically then required.

The 2-nitro-3-phenylbenzofuranyl cyanides for use in process C can be prepared by nitration of 2-unsubstituted or 2-halo-3phenylbenzofuranyl cyanides. These cyanides are readily hydrolyzed by conventional acid hydrolysis.

The 2-nitro-3-phenylbenzofurancarboxylic acid esters can also be prepared by nitration of 2-unsubstituted or 2-halo compounds or by esterification of 2-nitro-3-phenylbenzofurancarboxylic acid derivatives such as acyl halides with alcohols or acid salts with alkyl halides. These esters are readily hydrolyzed by conventional acid hydrolysis. Amides are prepared from the acid halide and the appropriate amine or by aminolysis of an ester. Quaternary aminoalkylamides and esters are prepared by alkylation of appropriate aminoalkylamides or esters. The acyl halides of the 2-nitro-3-phenylbenzofurancarboxylic acids are readily prepared by reaction of the acid with thionyl chloride, generally in a non-reactive solvent such as dichloromethane or benzene.

The 3-phenylbenzofurancarboxylic acid intermediates are prepared from chloro- or bromo-3-phenylbenzofurans by displacement of halogen with cyanide followed by hydrolysis of the cyano group to the carboxylic acid group.

Chloro- and bromo-3-phenylbenzofurans are known and are described generally in U.S. Pat. No. 3,862,134. They are prepared, for example, by reaction of α-bromoacetophenone and substituted α-bromacetophenones with halogenated phenols followed by cyclization, e.g., in polyphosphoric acid. For use in the synthetic sequences of this invention halo is chlorine, bromine or iodine unless otherwise specifically noted.

The reaction of the halogen of chloro- or bromo-3-phenylbenzofurans with cyanide is generally carried out in a basic organic solvent such as pyridine or quinoline. The preferred cyanide is cuprous cyanide. Elevated temperatures of 100° to 250° C are used to obtain satisfactory rates of reaction, although the temperature used should not be so high as to decompose the benzofuran ring.

Hydrolysis of the cyano group may be carried out under basic or acidic conditions. The extent of hydrolysis to the desired product is readily determined since the product is an acid and has significantly different solubility properties than the starting material.

The preparation of compounds wherein X or Y is chlorine requires that the halogen to be replaced by cyano be more reactive than chlorine, i.e., bromine, or that an alternative synthetic route be chosen.

The intermediate compounds of the formula

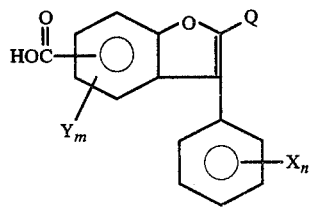

wherein X is fluorine, chlorine, lower alkyl or lower alkoxy, $n$ is 0, 1 or 2, Y is methyl, methoxy, fluorine or chlorine and Q is hydrogen, bromine or iodine, or an ester, amide, acid halide or pharmaceutically acceptable salt thereof are novel.

The salts of the free acid compounds of the invention are readily prepared by reaction of the acid with a base and evaporation to dryness. The base used to prepare the salts may be organic, e.g. sodium methoxide or an amine, or inorganic. Furthermore, other salts which are not pharmaceutically acceptable may be useful for the synthesis of the free acid compounds or other acceptable salts or other useful intermediates such as esters. The free acids can also be prepared from the corresponding esters by methods known to those skilled in the art.

The antimicrobial activity of the compounds is evaluated using a variation of the original agar-plate diffusion method of Vincent and Vincent (e.g. see Vincent, J. G., and Vincent, Helen W., Proc. Soc. Exptl. Biol. Med. 55:162–164, 1944, and Davis, B. D., and Mingioli, E. S., J. Bac. 66:129–136, 1953). Using this test, the compounds of the invention have been found to have a broad spectrum of activity against both gram-positive and gram-negative bacteria. The procedure provides information on the amount of a compound required to give complete inhibition, partial inhibition or no inhibition of microbial growth on agar plates. The microbial growth on each plate is read visually, and minimal inhibitory concentrations are recorded.

The microorganisms used are: *Staphylococcus aureus, Bacillus subtilus, Pseudomonas aeruginosa, Escherichi coli, Streptococcus sp.* (strains isolated from dental caries in rats or hamsters at the National Institute of Dental Health and grown in PFY or APT agar), *Asperigillus niger, Candida albicans, Mima polymorpha, Herellea vaginicola, Klebsiella pneumoniae* and *Streptococcus fecaelis.*

These are selected representatives of various bacterial and fungal classes and broad spectrum activity can be predicted as a result of activity against them. All of the compounds of the invention possess antimicrobial activity towards one or more of the above microorganisms. The compounds maintain high activity agains the microorganisms either in the absence or presence of 10 percent horse serum.

The in vivo antimicrobial activity is determined against infections produced by *Streptococcus pyogenes* C-203, and *Staphylococcus aureus* (Smith) or other bacterial species. The species used is determined by the in vitro antimicrobial spectrum of the compound. Groups of 5 or 10 mice, 18–22 g., are infected intrapertioneally with the test culture. Treatment consists of three oral injections 1, 6 and 24 hours after infection. All mice are observed for extended periods, e.g. for 2 weeks and deaths recorded at daily intervals. Control groups consist of one infected, nontreated group and other infected groups receiving varying dosages of the reference standard.

The acute oral toxicity of the compounds of the invention generally is moderate to low compared with the effective oral dose, and they have a good to excellent therapeutic ratio.

The compounds of the invention may be formulated by incorporating them into conventional pharmaceutical carrier materials, either organic or inorganic, which are suitable for oral or intraperitoneal application. For in vitro or topical use, simple aqueous solutions or suspensions are most conveniently employed. For this purpose, concentrations of the order of 100 parts per million up to about 5 parts per thousand are suitable, and the formulation is used by immersing an object to be treated therein, or by local application to an infected area. The amount of compound to be used for, e.g. oral treatment of a microbial infection will be an effective amount less than a toxic amount. The amount to be administered to a subject and route of administration to control an infection will depend on the species of organism, the sex, weight, physical condition of the patient, the locus of the infection and many other factors, but this judgement is well within the skill of the art. Usually the amount will be less than 100 mg/kg per dose. Conveniently the oral treatment is administered in the form of one of the usual pharmaceutical preparations such as capsules, tablets, emulsions, solutions, suppositories and the like. Excipients, fillers, coatings, etc., are employed with tablets or capsules, as is well known in the art.

It is often advantageous to combine the compounds of this invention with other antimicrobial compounds such as coccidiostats, anthelmintics, antifungals, antibiotics, steroids, or antibacterial agents, or to combine more than one compound described herein in a single composition.

Certain of the compounds are also active antiparasitics as shown by activity in laboratory tests versus the protozoan *Trichomonas sp.* In view of the outstanding antimicrobial activity of the compounds, they would also be expected to be effective growth promoters in various animal and bird species.

The following examples are given for the purpose of further illustrating the procedures of the present invention, but are not intended, in any way, to be limiting on the scope thereof. Thus, while the majority of the examples relate to the free acid compounds, the other compounds of the invention can also be prepared. The melting points are uncorrected, the temperatures are in degrees Centigrade and the pressures in millimeters of mercury.

EXAMPLE 1

A mixture of 123 g (0.45 mole) of 5-bromo-3-phenylbenzofuran, 50.3 g (0.562 mole) of cuprous cyanide and 30 ml of pyridine is heated at 150°–175° C for about 7 hours, then poured into a solution of 108 g of anhydrous ferric chloride, 67 ml of concentrated hydrochloric acid and 300 ml of water. The mixture is warmed without boiling for about 1 hour, then the solid is collected and washed with 6N hydrochloric acid and water. The product is stirred in 3 l of benzene for 1 hour, the benzene solution if filtered, and the filtrate is washed with 6N hydrochloric acid, water, 10% sodium hydroxide solution and saturated sodium chloride solution, then dried over magnesium sulfate. The solvent is then removed by evaporation to provide the product as a tan solid, mp 107°–116° C. An infrared spectrum of the product is consistent with the assigned structure, 5-cyano-3-phenylbenzofuran.

Using the method of Example 1 the following intermediates are prepared.

4-Cyano-3-phenylbenzofuran
7-cyano-3-phenylbenzofuran
7-cyano-5-fluoro-3-phenylbenzofuran
7-cyano-4-methoxy-3-phenylbenzofuran
7-cyano-5-methyl-3-phenylbenzofuran
7-cyano-3-(3,4-dimethylphenyl)benzofuran
7-cyano-3-(4-methoxyphenyl)benzofuran
5-cyano-3-(3-chlorophenyl)benzofuran
5-cyano-3-(4-fluorophenyl)benzofuran

EXAMPLE 2

A mixture of 76.2 g of 6-chloro-3-phenylbenzofuran, 34.1 g of cuprous cyanide and 28 ml of pyridine is heated for about 125 hours at a temperature of 200° C. The mixture is then poured into a solution of 100 g of ferric chloride in 60 ml of concentrated hydrochloric acid and 300 ml of ice water. The mixture is extracted twice with diethyl ether, the ether extracts are washed with saturated sodium chloride solution and dried. The solvent is evaporated to provide the desired product, 6-cyano-3-phenylbenzofuran.

EXAMPLE 3

A mixture of 90 g (0.411 mole) of 5-cyano-3-phenylbenzofuran, 90 g of 85% potassium hydroxide and 900 ml of 95% aqueous ethanol is heated to its reflux temperature and maintained at reflux for about 16 hours. The solvent is removed by evaporation and the residue is diluted with water and diethyl ether. The aqueous layer is separated and poured into cold dilute hydrochloric acid. A solid precipitates and is collected by filtration and washed with water. The product is then dissolved in diethyl ether. The ether solution is washed with water and saturated sodium chloride solution, then dried over sodium sulfate. The solvent is removed by evaporation to provide a solid which is recrystallized from aqueous ethanol then from a benzenehexane mixture to provide solid light tan needles of 3-phenyl-5-benzofurancarboxylic acid, m.p. 205°–290° C.

Using the method of Example 3 the following compounds are prepared.

3-phenyl-7-benzofurancarboxylic acid, m.p. 215°–216° C.
3-phenyl-4-benzofurancarboxylic acid
5-fluoro-3-phenyl-7-benzofurancarboxylic acid
4-methoxy-3-phenyl-7-benzofurancarboxylic acid
5-methyl-3-phenyl-7-benzofurancarboxylic acid
3-(3,4-dimethylphenyl)-7-benzofurancarboxylic acid
3-(4-methoxyphenyl)-7-benzofurancarboxylic acid
3-(3-chlorophenyl)-7-benzofurancarboxylic acid
3-(4-fluorophenyl)-7-benzofurancarboxylic acid

EXAMPLE 4

A mixture of 54.7 g of 6-cyano-3-phenylbenzofuran, 200 ml of acetic acid and 100 ml of hydrochloric acid is heated to its reflux temperature and maintained at reflux for about 20 hours. An additional 100 ml of hydrochloric acid is added and the mixture is refluxed further for about 27 hours. The reaction mixture is then added to water and the aqueous solution is extracted with diethyl ether. The ether layer is extracted with dilute sodium hydroxide solution. The basic aqueous solution is acidified with 6N hydrochloric acid and the solid precipitate is collected by filtration. The solid is recrystallized from aqueous ethanol to provide 3-phenyl-6-benzofurancarboxylic acid, m.p. 160°–170° C.

| Analysis: | %C | %H |
|---|---|---|
| Calculated for $C_{15}H_{10}O_3$: | 75.6 | 4.2 |
| Found: | 75.9 | 4.2 |

EXAMPLE 5

A mixture of 89 g (0.374 mole) of 3-phenyl-5-benzofurancarboxylic acid, 59.8 g (0.374 mole) of bromine and 2 l of dichloromethane is heated to its reflux temperature. A substantial amount of material does not dissolve. The reaction mixture is filtered. The filtrate is heated to reflux and 41 g (0.256 mole) of bromine diluted with 20 ml of dichloromethane is added dropwise to the refluxing solution. After a total reflux time of about 4 hours, the mixture is allowed to cool gradually, then filtered to provide a solid product. Infrared spectral analysis of the product confirms that it is 2-bromo-3-phenyl-5-benzofurancarboxylic acid, m.p. 265°–273° C.

EXAMPLE 6

Using the method of example 5, 3-phenyl-7-benzofurancrboxylic acid is converted to 2-bromo-3-phenyl-7-benzofurancarboxylic acid, m.p. 241°–243° C.

| | Analysis: | %C | %H |
|---|---|---|---|
| Calculated for $C_{15}H_9BrO_3$: | | 56.8 | 2.9 |
| Found: | | 56.9 | 2.8 |

Using the method of example 5 the following compound is prepared: 2-bromo-3-phenyl-4-benzofurancarboxylic acid.

EXAMPLE 7

A mixture of 20 g (0.063 mole) of 2-bromo-3-phenyl-5-benzofurancarboxylic acid and 1.25 l of acetic acid is stirred and heated to 55° C. To this mixture is added 7.7 g (0.094 mole) of cyclohexene. To this mixture is added dropwise 8.7 g (0.094 mole) of dinitrogen tetroxide in 25 ml of acetic acid. After 5 hours the mixture is poured into cold water and the solid product is collected. Recrystallization from aqueous ethanol followed by recrystallization from a benzene-ethanol mixture provides 2-nitro-3-phenyl-5-benzofurancarboxylic acid, m.p. 271°–273° C.

| | Analysis: | %C | %H | %N |
|---|---|---|---|---|
| Calculated for $C_{15}H_9NO_5$: | | 63.6 | 3.2 | 4.9 |
| Found: | | 63.4 | 3.5 | 4.8 |

EXAMPLE 8

A mixture of 2.2 g (0.007 mole) of 2-bromo-3-phenyl-7-benzofurancarboxylic acid and 50 ml of acetic acid is heated on a steam bath for 45 minutes to facilitate dissolution. To this mixture is added 2 ml of nitric acid, then 0.96 g (0.0139 mole) of sodium nitrite while stirring the mixture rapidly at about 80°–90° C. After stirring for about 45 minutes the mixture is poured into water. The solid is separated by filtration and recrystallized from ethanol to provide 2-nitro-3-phenyl-7-benzofurancarboxylic acid, m.p. 271°–272° C.

| | Analysis: | %C | %H | %N |
|---|---|---|---|---|
| Calculated for $C_{15}H_9NO_5$: | | 63.6 | 3.2 | 4.9 |
| Found: | | 63.5 | 3.1 | 4.8 |

EXAMPLE 9

A solution of 2 g of 3-phenyl-6-benzofurancarboxylic acid in 100 ml of dichloromethane and 20 drops of acetic acid is treated with 3.0 g of dinitrogen tetroxide. The mixture is stirred for about 70 hours then evaporated to provide a residue. The residue is treated with cold 5% sodium hydroxide solution until solution occurs. The solution is acidified with 6N hydrochloric acid and the yellow solid is collected and recrystallized from ethanol to provide 2-nitro-3-phenyl-6-benzofurancarboxylic acid, m.p. 244°–247° C.

| | Analysis: | %C | %H | %N |
|---|---|---|---|---|
| Calculated for $C_{15}H_9NO_5$: | | 63.6 | 3.2 | 4.9 |
| Found: | | 63.5 | 3.2 | 4.9 |

EXAMPLE 10

A mixture of 28.3 g (0.10 mole) of 2-nitro-3-phenyl-7-benzofurancarboxylic acid and 100 ml of thionyl chloride in 100 ml of benzene is heated to reflux and refluxed for 1.5 hours, then evaporated to provide a solid residue of 2-nitro-3-phenyl-7-benzofurancarboxyl chloride, m.p. 146°–149° C.

EXAMPLE 11

To a solution of 5.1 g (0.05 mole) of N,N-dimethylamino-3-aminopropane in 100 ml of benzene is added dropwise a solution of 2-nitro-3-phenyl-7-benzofurancarboxyl chloride in 100 ml of benzene. The mixture is stirred for 3.5 hours, cooled with an ice bath and filtered. The filtrate is washed thrice with water, twice with saturated sodium chloride solution, once with saturated sodium bicarbonate solution and twice with saturated sodium chloride solution, then dried, treated with decolorizing charcoal and filtered. Evaporation provides an oil which is triturated with petroleum ether to give a precipitate. Recrystallization twice from a cyclohexane-benzene mixture provides N,N-dimethylaminopropyl-2-nitro-3-phenyl-7-benzofurancarboxamide, m.p. 85°–88° C.

| | Analysis: | %C | %H | %N |
|---|---|---|---|---|
| Calculated for $C_{20}H_{21}N_3O_4$: | | 65.4 | 5.8 | 11.5 |
| Found: | | 65.1 | 5.8 | 11.6 |

Using the method of Example 11 2-nitro-3-phenyl-7-benzofurancarboxyl chloride is reacted with various amines shown below to provide the products illustrated.

Table I

| Example No. | Product | Melting Point (in ° C) |
|---|---|---|
| 12 | N,N-bis(2-hydroxyethyl)-2-nitro-3-phenyl-7-benzofurancarboxamide | 159–161 |
| 13 | N,N-bis(N',N'-dimethylaminoethyl)-2-nitro-3-phenyl-7-benzofurancarboxamide | 151–153 |
| 14 | 2-nitro-3-phenyl-7-benzofurancarboxamide | 267–269 |
| 15 | N-(5-tetrazolyl)-2-nitro-3-phenyl-7-benzofurancarboxamide | 300 |
| 16 | ethyl N-(2-nitro-3-phenyl-7-benzofuranylglycinate | 178–180 |
| 17 | 4-(2-nitro-3-phenyl-7-benzofuranylcarboxamido)-benzoic acid | 308–311 |
| 18 | sodium 2-nitro-3-phenyl-7-benzofuranylcarboxamidoethanesulfonate | >325 |
| 19 | 4-(2-nitro-3-phenyl-7-benzofurancarboxamido)-benzenesulfonamide | 280–281.5 (dec.) |
| 20 | 1-(2-nitro-3-phenyl-7-benzofuranoyl)-4-methylpiperazine | 229–231 |
| 21 | 2-nitro-3-phenyl-7-benzofuranylpenicillin sodium salt | 240–245 (dec.) |
| 22 | ethyl 4-(2-nitro-3-phenyl-7- | 168–171 |

Table I-continued

| Example No. | Product | Melting Point (in °C) |
|---|---|---|
| | benzofurancarboxamide)benzoate | |

EXAMPLE 23

The compound of Example 21 is dissolved in methanol and stirred with cold sodium methoxide for 1 hour. Diethyl ether is added and the precipitate separated by filtration. The product is 2-nitro-3-phenyl-7-carboxamidopenicilloic acid monomethyl ester monosodium salt hydrate m.p. 191°–196° C. (dec.).

EXAMPLE 24

Ethyl N-(2-nitro-3-phenyl-7-benzofuranoyl)glycinate is hydrolyzed by stirring in ethanolic sodium hydroxide solution to provide N-(2-nitro-3-phenyl-7-benzofuranoyl)glycine, m.p. 123°–126° C.

| Analysis: | %C | %H | %N |
|---|---|---|---|
| Calculated for $C_{17}H_{12}N_2O_6$: | 60.0 | 3.6 | 8.2 |
| Found: | 60.2 | 3.5 | 8.2 |

EXAMPLE 25

A mixture of 14.2 g (0.05 mole) of 2-nitro-3-phenyl-7-benzofurancarboxylic acid, 8.6 g (0.05 mole) of N,N-diethylamino-2-chloroethane hydrochloride, 10.1 g (0.1 mole) of triethylamine and 75 ml of N,N-dimethylformamide is heated at 90° to 100° C. for 16 hours, then left standing at 23° C. for 2 days. The mixture is cooled with an ice bath, then filtered to remove the white solid by-product. The filtrate is dissolved in diethyl ether, washed thrice with water and twice with saturated sodium chloride solution and dried. The solution is evaporated to provide an oil, N,N-diethylaminoethyl 2-nitro-3-phenyl-7-benzofurancarboxylate. This oil is dissolved in diethyl ether and treated with 25 ml of 4N-hydrochloric acid in isopropanol to provide a product which gradually solidifies. The product is recrystallized twice from ethanol to provide, N,N-diethylaminoethyl 2-nitro-3-phenyl-7-benzofurancarboxylate hydrochloride, m.p. 194.5°–195° C., as a light yellow solid.

| Analysis: | %C | %H | %N |
|---|---|---|---|
| Calculated for $C_{21}H_{22}N_2O_5 \cdot HCl$: | 60.2 | 5.5 | 6.7 |
| Found: | 60.2 | 5.4 | 6.6 |

EXAMPLE 26

Using the method illustrated in Example 25 N,N-dimethylamino-3-chloropropane hydrochloride is reacted with 2-nitro-3-phenyl-7-benzofurancarboxylic acid to provide N,N-dimethylaminopropyl 2-nitro-3-phenyl-7-benzofurancarboxylate, m.p. 65.5°–67.5° C., as a yellow solid.

EXAMPLE 27

A solution of 4.0 g (0.0011 mole) of N,N-dimethylaminopropyl 2-nitro-3-phenyl-7-benzofurancarboxylate in 10 ml of ethanol is treated with 0.4 g of methyl iodide and the solution is stirred for 30 minutes. Diethyl ether is added to the solution and a solid precipitate forms and is separated by filtration. The product is recrystallized from methanol to provide (2-nitro-3-phenyl-7-benzofuranylcarboxypropyl)trimethylammonium iodide, m.p. 246° C. (dec.).

| Analysis: | %C | %H | %N |
|---|---|---|---|
| Calculated for $C_{21}H_{23}IN_2O_5$: | 49.45 | 4.55 | 5.5 |
| Found: | 49.30 | 4.70 | 5.5 |

EXAMPLE 28

Using the method of Example 27, N,N-dimethylaminopropyl-2-nitro-3-phenyl-7-benzofurancarboxylamide is reacted with methyl iodide to provide (2-nitro-3-phenyl-7-benzofuranylcarboxamidopropyl)-trimethylammonium iodide, m.p. 178.5°–181° C. (dec.).

| Analysis: | %C | %H | %N |
|---|---|---|---|
| Calculated for $C_{21}H_{24}IN_3O_4$: | 49.6 | 4.8 | 8.3 |
| Found: | 49.5 | 4.8 | 8.3 |

Using the method of Example 9 the following compounds are prepared:

TABLE II

Example 29: 5-fluoro-2-nitro-3-phenyl-7-benzofurancarboxylic acid

Example 30: 4-methoxy-2-nitro-3-phenyl-7-benzofurancarboxylic acid

Example 31: 5-methyl-2-nitro-3-phenyl-7-benzofurancarboxylic acid

Example 32: 3-(3,4-dimethylphenyl)-3-phenyl-7-benzofurancarboxylic acid

Example 33: 3-(4-methoxyphenyl)-3-phenyl-7-benzofurancarboxylic acid

Example 34: 3-(3-chlorophenyl)-3-phenyl-7-benzofurancarboxylic acid

Example 35: 3-(4-fluorophenyl)-3-phenyl-7-benzofurancarboxylic acid.

Using the method of Example 9 the following intermediates are prepared starting with intermediates of Examples 1 and 2:

TABLE III

Example 36: 5-cyano-3-phenyl-2-nitrobenzofuran

Example 37: 7-cyano-3-phenyl-2-nitrobenzofuran

Example 38: 6-cyano-3-phenyl-2-nitrobenzofuran

Example 39: 7-cyano-5-fluoro-3-phenyl-2-nitrobenzofuran

Example 40: 7-cyano-4-methoxy-3-phenyl-2-nitrobenzofuran

Example 41: 7-cyano-5-methyl-3-phenyl-2-nitrobenzofuran

Example 42: 7cyano-3-(3,4-dimethylphenyl)-2-nitrobenzofuran

Example 43: 7-cyano-3-(4-methoxyphenyl)-2-nitrobenzofuran

Example 44: 5-cyano-3-(3-chlorophenyl)-2-nitrobenzofuran

Example 45: 5-cyano-3-(4-fluorophenyl)-2-nitrobenzofuran

What is claimed is:

1. A compound of the formula

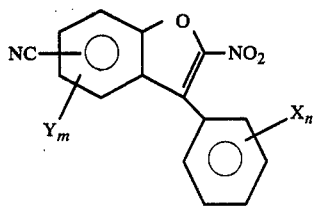

wherein X is fluorine, chlorine, lower alkyl or lower alkoxy, Y is methyl, methoxy, fluorine or chlorine and $m$ and $n$ are independently 0, 1 or 2.

2. 5-Cyano-3-phenyl-2-nitrobenzofuran according to claim 1.

3. 7-Cyano-3-phenyl-2-nitrobenzofuran according to claim 1.

4. 6-Cyano-3-phenyl-2-nitrobenzofuran according to claim 1.

5. 7-Cyano-5-fluoro-3-phenyl-2-nitrobenzofuran according to claim 1.

6. 7-Cyano-4-methoxy-3-phenyl-2-nitrobenzofuran according to claim 1.

7. 7-Cyano-5-methyl-3-phenyl-2-nitrobenzofuran according to claim 1.

8. 7-Cyano-3-(3,4-dimethylphenyl)-2-nitrobenzofuran according to claim 1.

9. 7-Cyano-3-(4-methoxyphenyl)-2-nitrobenzofuran according to claim 1.

10. 5-Cyano-3-(3-chlorophenyl)-2-nitrobenzofuran according to claim 1.

11. 5-Cyano-3-(4-fluorophenyl)-2-nitrobenzofuran according to claim 1.

* * * * *